(12) United States Patent
Martone et al.

(10) Patent No.: US 7,081,097 B2
(45) Date of Patent: Jul. 25, 2006

(54) ENDOSCOPE SHEATH ASSEMBLIES HAVING AN ATTACHED BIOPSY SAMPLING DEVICE

(75) Inventors: Stephen Martone, Westford, MA (US); Katsumi Oneda, Alpine, NJ (US)

(73) Assignee: Vision Sciences, Inc., Natick, MA (US)

( * ) Notice: Subject to any disclaimer, the term of this patent is extended or adjusted under 35 U.S.C. 154(b) by 263 days.

(21) Appl. No.: 10/040,923

(22) Filed: Jan. 4, 2002

(65) Prior Publication Data

US 2004/0059253 A1    Mar. 25, 2004

(51) Int. Cl.
*A61B 10/00*    (2006.01)
*A61B 1/00*    (2006.01)

(52) U.S. Cl. ............... 600/562; 600/569; 600/127; 600/104; 600/121

(58) Field of Classification Search ........... 600/107, 600/108, 186, 127, 104, 129, 121, 562, 569, 600/105, 106, 123, 570, 566, 567
See application file for complete search history.

(56) References Cited

U.S. PATENT DOCUMENTS

| | | | |
|---|---|---|---|
| 4,651,753 A | 3/1987 | Lifton | 128/751 |
| 4,676,229 A | 6/1987 | Krasnicki et al. | 128/4 |
| 4,714,075 A | 12/1987 | Krauter et al. | 128/4 |
| 4,793,326 A * | 12/1988 | Shishido | 356/241.4 |
| 5,146,928 A | 9/1992 | Esser | 128/756 |
| 5,301,061 A * | 4/1994 | Nakada et al. | 359/362 |
| 5,337,734 A * | 8/1994 | Saab | 600/121 |
| 5,417,697 A | 5/1995 | Wilk et al. | 606/113 |
| 5,419,310 A | 5/1995 | Frassica et al. | 128/4 |
| 5,483,951 A | 1/1996 | Frassica et al. | 600/104 |
| 5,503,616 A | 4/1996 | Jones | 600/155 |
| 5,535,759 A | 7/1996 | Wilk | 128/898 |
| 5,603,699 A * | 2/1997 | Shine | 604/110 |
| 5,741,271 A | 4/1998 | Nakao et al. | 606/114 |
| 5,746,692 A * | 5/1998 | Bacich et al. | 600/104 |
| 5,759,187 A | 6/1998 | Nakao et al. | 606/114 |
| 5,762,069 A | 6/1998 | Kelleher et al. | 128/751 |
| 5,820,630 A | 10/1998 | Lind | 606/208 |
| 5,899,850 A * | 5/1999 | Ouchi | 600/104 |
| 5,906,630 A | 5/1999 | Anderhub et al. | 606/205 |
| 5,931,833 A | 8/1999 | Silverstein | 606/1 |
| 5,938,586 A | 8/1999 | Wilk et al. | 600/123 |
| 5,997,547 A | 12/1999 | Nakao et al. | 606/114 |
| 6,203,493 B1 | 3/2001 | Ben-Haim | 600/117 |
| 6,309,345 B1 | 10/2001 | Stelzer et al. | 600/106 |
| 6,551,278 B1* | 4/2003 | Geitz | 604/131 |
| 6,699,178 B1* | 3/2004 | Koda | 600/104 |

\* cited by examiner

*Primary Examiner*—Charles Marmor
*Assistant Examiner*—Jonathan Foreman
(74) *Attorney, Agent, or Firm*—Dorsey & Whitney LLP

(57) ABSTRACT

Apparatus and methods for obtaining biopsy samples using an endoscope assembly are disclosed. In one embodiment, an assembly adapted for use with an endoscopic insertion tube includes a sheath having a body portion adapted to at least partially encapsulate a distal portion of the insertion tube, and a biopsy sampling device attached to the sheath and including a collection member proximate an end of the body portion. The biopsy sampling device may be attached to the body portion of the sheath, or alternately, may be attached to an enclosed distal end of the sheath. The assembly may also include a cover attached to the sheath and positionable proximate the biopsy sampling device. An actuation member may be attached to the cover and may extend along the sheath, allowing the operator to actuate the cover between a covered position and a collecting position.

19 Claims, 7 Drawing Sheets

ENDOSCOPE SHEATH ASSEMBLIES HAVING AN ATTACHED BIOPSY SAMPLING DEVICE

TECHNICAL FIELD

The present invention is directed toward apparatus and methods for obtaining biopsy samples using an endoscope, and more specifically, to endoscope sheath assemblies having an attached biopsy sampling device.

BACKGROUND OF THE INVENTION

Endoscopes are widely used for a variety of medical procedures. To improve their performance, endoscopes have been optimized in various ways to best accomplish their purpose. Examples of specialized endoscopes include angioscopes, colonoscopes, bronchoscopes, and arthroscopes.

One of the medical procedures that may be performed using an endoscope is obtaining a biopsy sample. FIG. 1 shows a conventional endoscope assembly 10 used for obtaining a biopsy sample. The endoscope assembly 10 includes an endoscope 20 having an elongated insertion tube 22. The insertion tube 22 may be rigid, partially flexible, or entirely flexible. The insertion tube 22 includes a distal portion 24 that may be inserted into a body cavity of a patient (not shown), and a working end 26.

The endoscope 20 includes a headpiece 28 that remains external to the patient during a medical procedure. In the embodiment shown in FIG. 1, the headpiece 28 includes an eyepiece 30 for viewing the scene through a viewing lens 31 at the working end 26 of the insertion tube 22, a pair of bending control knobs 32 for manipulating the position of the distal portion 24 of the insertion tube 22, and a pair of fluid control actuators 34 for controlling the flow of fluids through tubes 36 to (or from) the working end 26. Endoscopes 20 of the type generally shown in FIG. 1 are described more fully, for example, in U.S. Pat. No. 5,931,833 issued to Silverstein, U.S. Pat. No. 5,483,951 issued to Frassica and Ailinger, and U.S. Pat. No. 4,714,075 issued to Krauter and Vivenzio, which patents are incorporated herein by reference. Representative commercially-available endoscopes include, for example, video or fiberoptically-equipped sigmoidoscopes, bronchoscopes, nasopharyngolaryngoscopes, colonoscopes, and gastroscopes.

As further shown in FIG. 1, the endoscope assembly 10 includes a sheath 40 that encapsulates the insertion tube 22 to prevent at least part of the insertion tube 22 from being soiled during the medical procedure. The sheath 40 may be flexible to allow unrestricted bending of the flexible portion of the insertion tube 22, or may be relatively rigid. In the depicted embodiment, the sheath 40 includes an enlarged fitting portion 42 that fits over an engagement portion 44 of the headpiece 28, and a channel 46 having a proximal end 48 that projects outwardly from the sheath 40 proximate the headpiece 28. Sheaths 40 of the type generally shown in FIG. 1 are described more fully, for example, in the above-referenced patent to Frassica and Ailinger.

During a medical procedure, a surgical instrument 50 having a biopsy sampling device 52 is inserted into the proximal end 48 of the channel 46, and slid through the channel 46 until the biopsy sampling device 52 emerges at the working end 26. A variety of biopsy sampling devices 52 are known, including forceps (e.g. U.S. Pat. No. 5,820,630 issued to Lind), loop and cup devices (e.g. U.S. Pat. No. 5,417,697 issued to Wilk et al., U.S. Pat. No. 5,741,271 issued to Nakao et al.), and cylindrical cutting devices (e.g. U.S. Pat. No. 4,651,753 issued to Lifton). In alternate embodiments, the biopsy sampling device 52 may be inserted through one or more channels that are integrated into the insertion tube 22 of the endoscope 20, as described, for example, in the above-referenced patents to Silverstein and Nakao et al. After a biopsy sample is obtained, the biopsy sampling device 52 containing the biopsy sample may be withdrawn through the channel 46, or alternately, the entire insertion tube 22 may be withdrawn from the patient's body with the biopsy sampling device 52 remaining in position near the working end 26.

Although desirable results may be achieved using conventional endoscope assemblies, some drawbacks exist. For example, in some fields of medicine, the majority of physicians do not own an endoscope having built-in channels due to the prohibitively high cost of such instruments. Although sheaths having channels may be used, some biopsy sampling devices are too large to be fitted through the conventionally-sized channels (typically 2 mm in diameter) of existing endoscope sheaths.

Furthermore, relatively new diagnostic techniques are available that allow for testing for the presence of cancer by testing cells that are obtained by brushing a mucosal surface using a biopsy brush. In some areas of the body (e.g. the mouth), a target surface may be readily accessible using an ordinary biopsy brush without the use of specialized tools. Other areas of the body (e.g. the nasopharynx or the esophagus), however, may not be reachable using an ordinary biopsy brush. Existing endoscope assemblies severely limit the sizes of biopsy brushes that may be employed due to the relatively small sizes of the channels, making the task of obtaining a suitable sample using a biopsy brush difficult or virtually impossible.

SUMMARY OF THE INVENTION

The present invention is directed to apparatus and methods for obtaining biopsy samples using an endoscope assembly. In one embodiment, an assembly adapted for use with an endoscopic insertion tube includes a sheath having a body portion adapted to at least partially encapsulate a distal portion of the insertion tube when the sheath assembly is positioned on the insertion tube, and a biopsy sampling device attached to the sheath and including a collection member. The biopsy sampling device may be attached to the body portion of the sheath, or alternately, may be attached to an enclosed distal end of the sheath. The biopsy sampling device may include a biopsy brush.

In an alternate embodiment, the assembly may include a cover attached to the sheath and positionable proximate the biopsy sampling device. The cover may be moveable (slideably, hingeably, etc.) between a first position proximate the biopsy sampling device, and a second position spaced apart from the biopsy sampling device. The cover may include an actuation member that extends along the body portion of the sheath, allowing the operator to actuate the cover between the first and second positions when the assembly is inserted into the body cavity of a patient.

DETAILED DESCRIPTION OF THE INVENTION

The present invention is directed toward apparatus and methods for obtaining biopsy samples using an endoscope, and more specifically, to endoscope sheath assemblies having an attached biopsy sampling device. Many specific details of certain embodiments of the invention are set forth in the following description and in FIGS. 2–11 to provide a thorough understanding of such embodiments. One skilled in the art, however, will understand that the present invention may have additional embodiments, or that the invention may be practiced without several of the details described in the following description.

Figure 1:
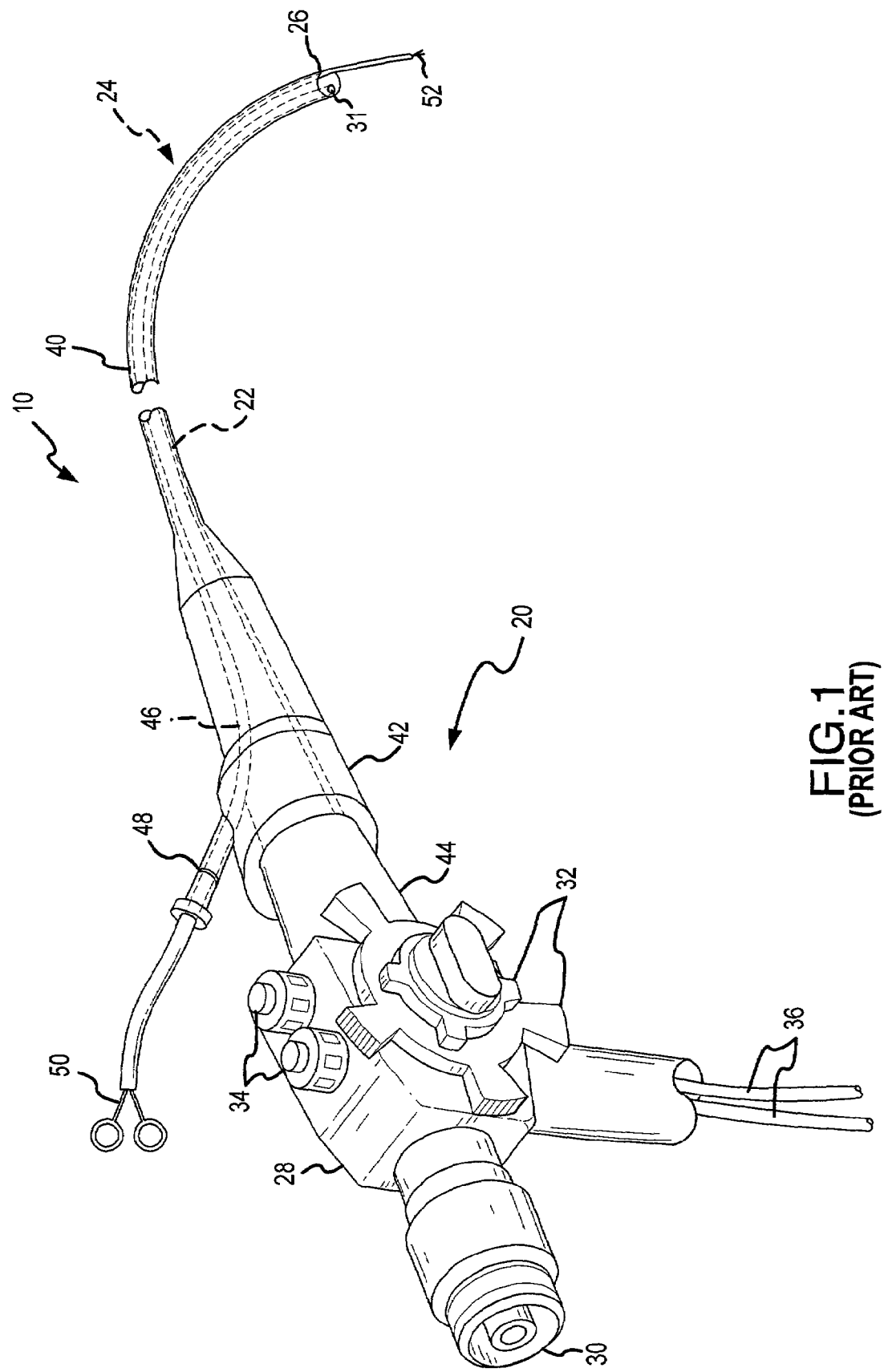
FIG. 1 is an isometric view of a prior art endoscope assembly.
Figure 2:
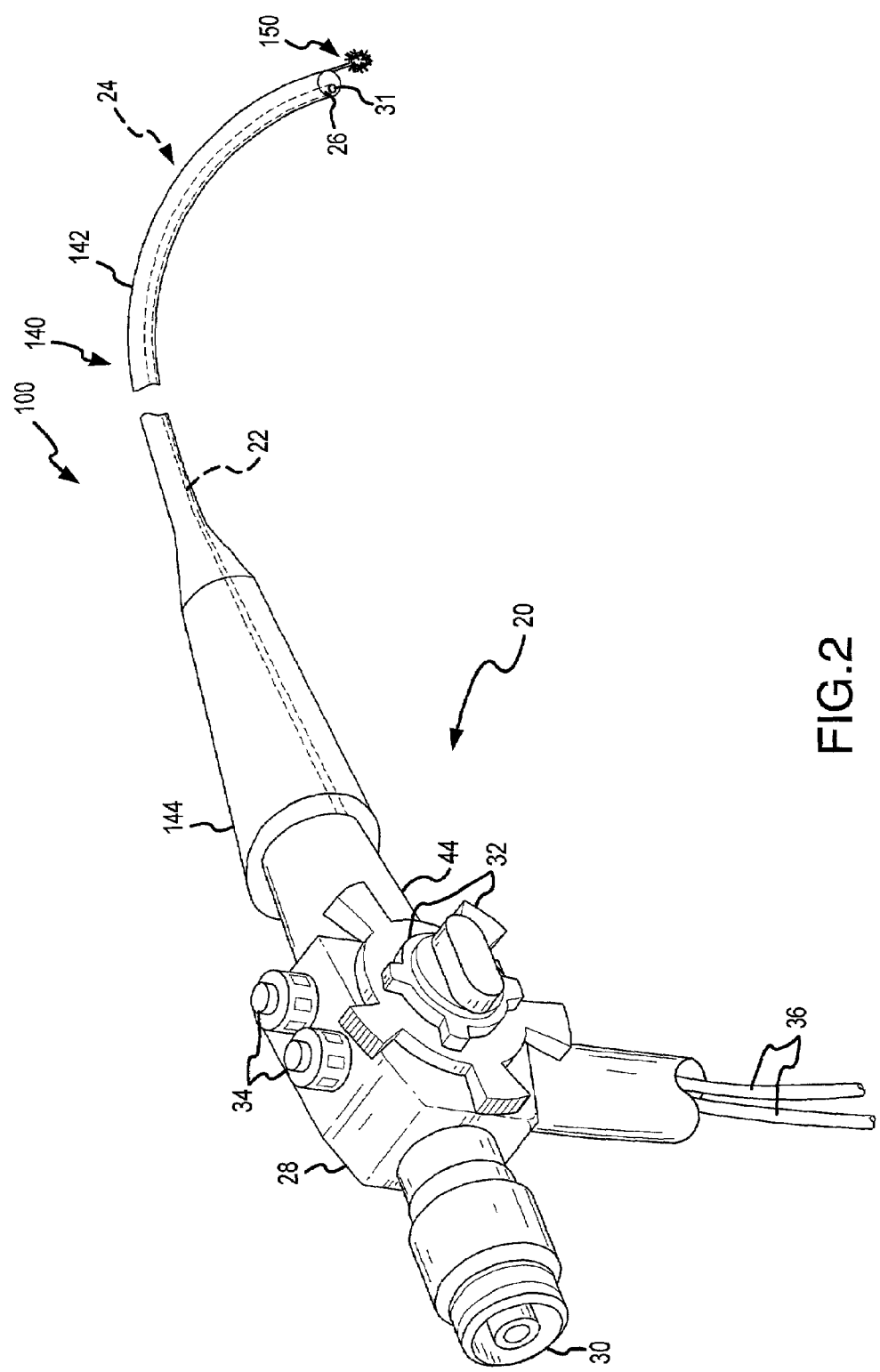
FIG. 2 is an isometric view of an endoscope assembly in accordance with an embodiment of the invention.

FIG. 2 is an isometric view of an endoscope assembly 100 in accordance with an embodiment of the invention. The endoscope assembly 100 includes an endoscope 20 and a sheath assembly 140 having a biopsy sampling device 150 attached thereto. The sheath assembly 140 having the attached biopsy sampling device 150 enables a physician to obtain a biopsy sample using an endoscope that does not have channels. Likewise, the requirement for channels to be attached to or included in the sheath is advantageously eliminated.

As described more fully above, and with continued reference to FIG. 2, the endoscope 20 includes an insertion tube 22 having a distal portion 24 that may be inserted into a body cavity of a patient (not shown). The distal portion 24 terminates in a working end 26 of the insertion tube 22. The sheath assembly 140 includes a generally tubular body portion 142 that at least partially encapsulates the distal portion 24 of the insertion tube 22, and a proximal fitting 144 having an enlarged diameter that fits onto an engagement portion 44 of the endoscope 20. The body portion 142 may be fabricated from a variety of flexible, elastomeric materials to permit unrestricted movement of the insertion tube 22, or may be constructed of a relatively inelastic material, as described, for example, in U.S. Pat. No. 5,337,734 issued to Saab. Furthermore, the body portion 142 may snugly surround the insertion tube 22 as shown in FIG. 2, or may loosely enclose the insertion tube 22 as disclosed, for example, in U.S. Pat. No. 5,386,817 issued to Jones.

Figure 3:
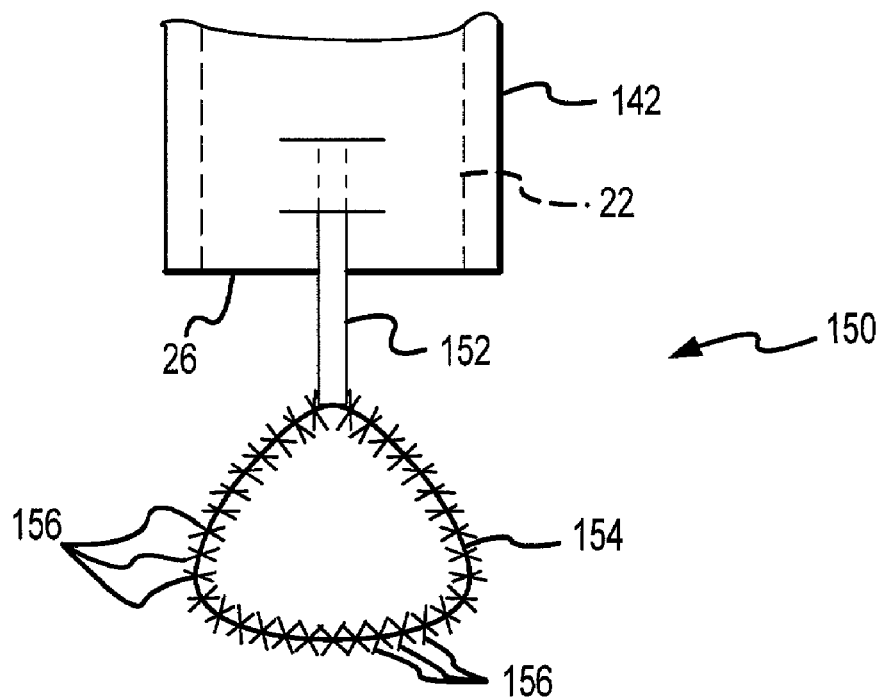
FIG. 3 is an enlarged side elevational view of a biopsy sampling device of the endoscope assembly of FIG. 2.

FIG. 3 is an enlarged side elevational view of the biopsy sampling device 150 of the endoscope assembly of FIG. 2.

As shown in FIG. 3, the biopsy sampling device 150 includes a base member 152 attached to an outer surface of the body portion 142 of the sheath assembly 140, and a collection member 154 attached to the base member 152. In this embodiment, the collection member 154 is a biopsy brush having a plurality of bristles 156 that contact the target and gather cells for subsequent analysis. In this embodiment, the collection member 154 projects beyond the working end 26 of the insertion tube 22.

In operation, the sheath assembly 140 is positioned on the endoscope with the body portion 142 surrounding the insertion tube 22. In the embodiment shown in FIGS. 2 and 3, the body portion 142 has an open end, and therefore, does not enclose the working end 26 of the insertion tube 22. In alternate embodiments, the body portion 142 may include an end cap that completely encloses the working end 26 and isolates the insertion tube 22 from contamination. The biopsy sampling device 150 and the distal portion 24 of the insertion tube 22 are then inserted into the body cavity of the patient. By looking through the eyepiece 30, the operator views the interior of the body cavity through the viewing lens 31 and maneuvers the working end 26 to a position proximate to the target. The biopsy sampling device 150 is then maneuvered into engagement with the target to obtain a biopsy sample. The insertion tube 22 and biopsy sampling device 150 are then removed from the body cavity, and the biopsy sample is removed from the collection member 154 for analysis.

The sheath assembly 140 having the attached biopsy sampling device 150 advantageously permits an operator to collect a biopsy sample using a simplified, less expensive assembly compared with prior art devices. Because the biopsy sampling device 150 is attached to the sheath assembly 140, there is no need for a relatively expensive endoscope having channels extending through the insertion tube 22, or for a sheath having channels. In addition to reducing the cost of the assembly, the costs of operating the endoscope assembly may be reduced because the necessity for cleaning the channels of an endoscope after performing a medical procedure is eliminated.

Also, because the collection member 154 is not inserted or retracted through a channel, the size of the collection member 154 may be increased compared with conventional devices wherein the size of the collection member is limited by the size of the channel. Thus, the inventive sheath assembly 140 advantageously permits a larger collection member 154 (e.g. biopsy brush) to be employed. Because a larger collection member 154 may be used, the likelihood of obtaining a suitable biopsy sample is improved, thereby reducing the possibility of increased costs and additional discomfort to the patient of performing repeated endoscopic procedures to obtain a suitable sample.

Figure 4:
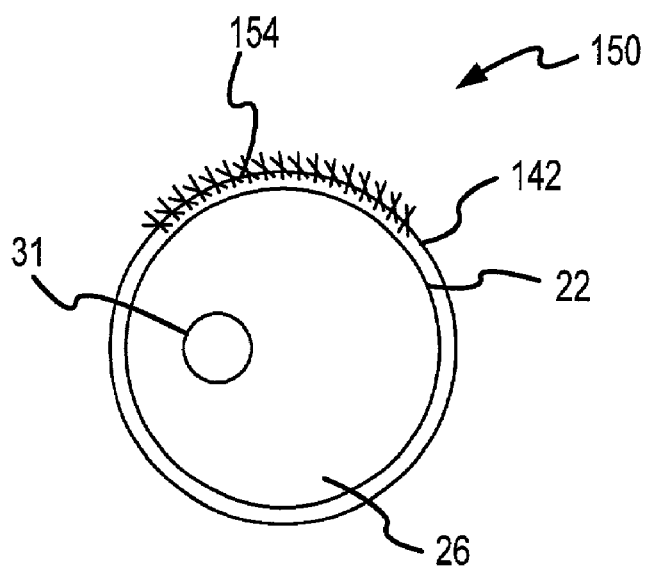
FIG. 4 is an enlarged end elevational view of the biopsy sampling device of the endoscope assembly of FIG. 2.

FIG. 4 is an enlarged end elevational view of the biopsy sampling device 150 of the endoscope assembly 100 of FIG. 2. As shown in FIG. 4, the collection member 154 has a curvature that closely conforms to the curvature of the cylindrical insertion tube 22. Because the collection member 154 has a curvature similar to that of the insertion tube 22, the sample-gathering surface area of the collection member 154 may be increased without significantly increasing the diameter of the assembly 100, and without significantly increasing the difficulty of inserting or removing the assembly 100 from the body cavity.

Several alternate embodiments of endoscope assemblies in accordance with the invention will be described below. Generally, in the following discussion, where the construction and operation of alternate embodiments is substantially similar to previously described embodiments, the common elements and features are identified by reference numbers which are the same or similar to those used above. Only significant differences in construction or operation are described in detail.

Figure 5:
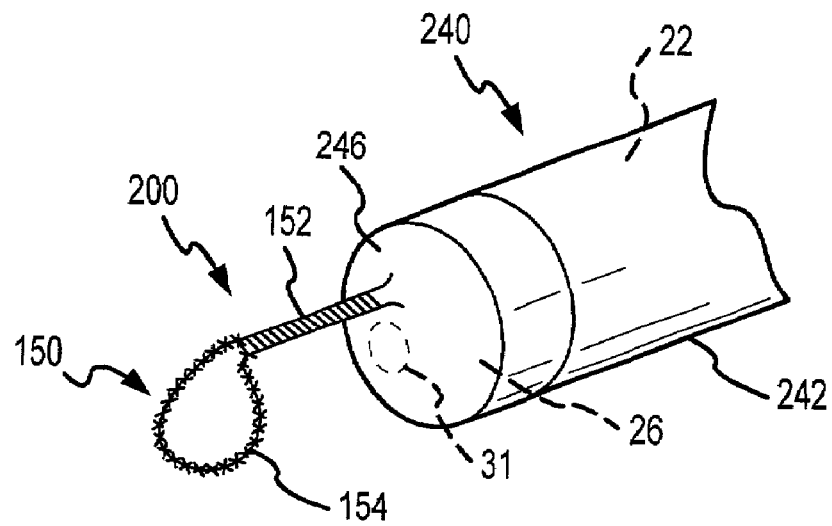
FIG. 5 is an enlarged, partial isometric view of a distal end of an endoscope assembly in accordance with an alternate embodiment of the invention.

FIG. 5 is an isometric view of a distal end of an endoscope assembly 200 in accordance with an alternate embodiment of the invention. In this embodiment, the sheath assembly 240 includes an enclosed end cap 246 that encloses the working end 26 of the insertion tube 22. The end cap 246 may be fabricated separately from the tubular body portion 242 of the sheath assembly 240 and then attached to the body portion 242 by a suitable attachment means, or it may be integrally formed with the tubular body portion 242 as disclosed, for example, in co-pending, commonly owned U.S. patent application Ser. No. 09/235,355, or in the above-referenced patent to Saab.

In the embodiment shown in FIG. 5, the base member 152 of the biopsy sampling device 150 is attached to the end cap 246. The base member 152 may be coupled to the end cap 246 in a variety of known ways, including attaching the base member 152 using an epoxy or other adhesive, threadedly engaging the base member 152 to a correspondingly-threaded receiving member on the end cap 246, or other suitable attachment means. Preferably, the base member 152 may be integrally formed with the end cap 246 to ensure a reliable attachment.

The endoscope assembly 200 provides the above-noted advantages of the previously described embodiments of the invention, and may also provide additional advantages. For example, because the biopsy sampling device 150 is attached to the end cap 246, the biopsy sampling device 150 may be designed such that it does not project beyond the outer diameter of the body portion 242 of the sheath assembly 240. This may result in improved ease of inserting and removing the endoscope assembly 200, and correspondingly less discomfort to the patient. Also, because the sheath assembly 240 includes an end cap 246, the sheath assembly 240 provides improved isolation of the insertion tube 22 from contaminants during a medical procedure, thereby reducing the operating costs of the endoscope assembly by reducing or eliminating labor-intensive cleaning procedures after a medical procedure is performed.

Figure 6:
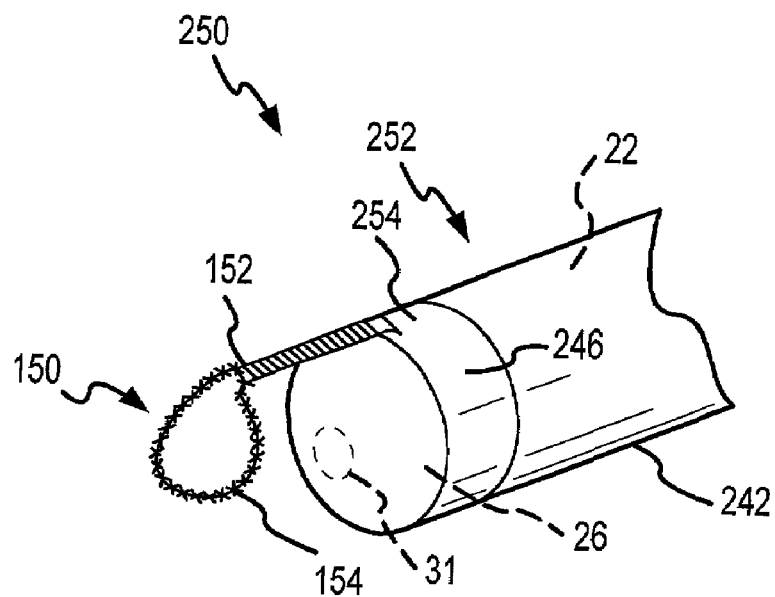
FIG. 6 is an enlarged, partial isometric view of a distal end of an endoscope assembly in accordance with another embodiment of the invention.

FIG. 6 is an enlarged, partial isometric view of a distal end of an endoscope assembly 250 in accordance with another embodiment of the invention. In this embodiment, the biopsy sampling device 150 is attached to an outer peripheral surface 254 of the end cap 246 of the sheath assembly 252. As described more fully above, the end cap 246 may be fabricated separately from the tubular body portion 242 and then attached to the body portion 242 by a suitable attachment means, or it may be integrally formed with the tubular body portion 242. The above-noted advantages of having the biopsy sampling device 150 attached to the sheath assembly 252 may also be achieved using the endoscope assembly 250 shown in FIG. 6.

Figure 7:
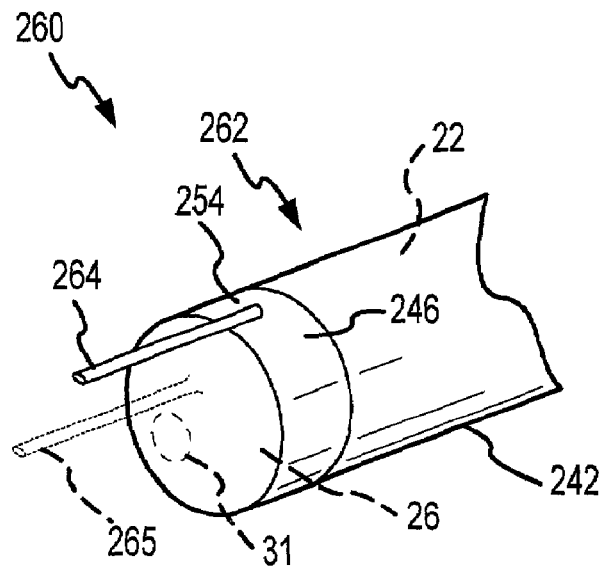
FIG. 7 is an enlarged, partial isometric view of a distal end of an endoscope assembly in accordance with yet another embodiment of the invention.

FIG. 7 is an enlarged, partial isometric view of a distal end of an endoscope assembly 260 in accordance with yet another embodiment of the invention. In this embodiment, a biopsy collection needle 264 is attached to the outer peripheral surface 254 of the end cap 246 of the sheath assembly 262. As shown in FIG. 7, in an alternate embodiment, a second biopsy collection needle 265 attached to the end surface of the end cap 246 may be employed instead of, or in addition to, the biopsy collection needle 264 attached to the outer peripheral surface 254.

The endoscope assembly 260 shown in FIG. 7 demonstrates that alternate embodiments of biopsy sampling devices may be attached to sheath assemblies according to the invention. For example, in further embodiments, the biopsy sampling device may be a forceps, a loop and cup device, a cylindrical cutting device, or any other suitable biopsy sampling apparatus. Furthermore, FIG. 7 also demonstrates that a plurality of biopsy sampling devices may be attached to sheath assemblies in accordance with the invention to achieve the advantages taught by the present disclosure.

Figure 8:
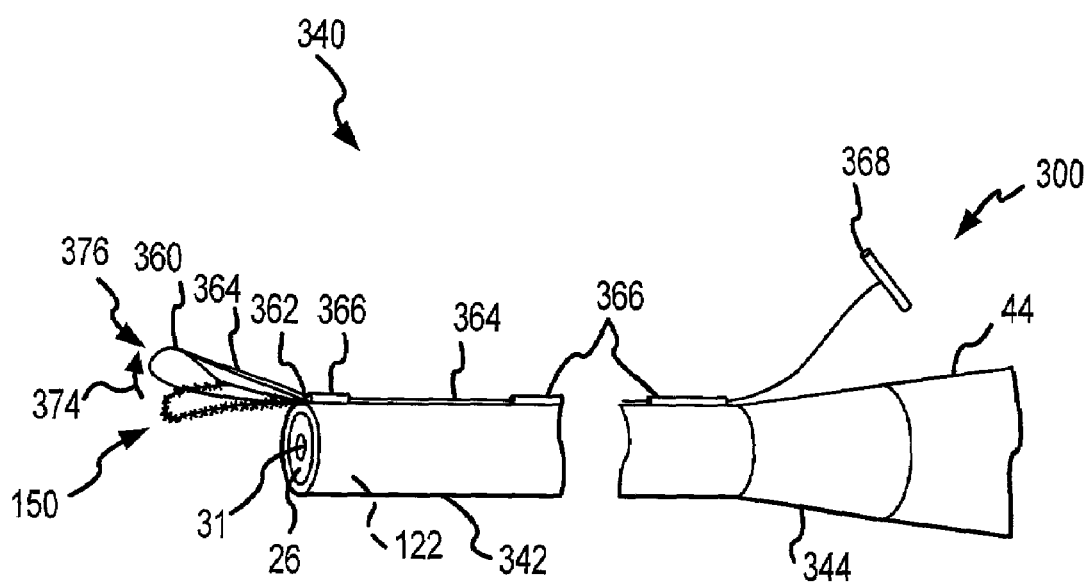
FIG. 8 is a partial isometric view of an endoscope assembly in accordance with another alternate embodiment of the invention.
Figure 9:
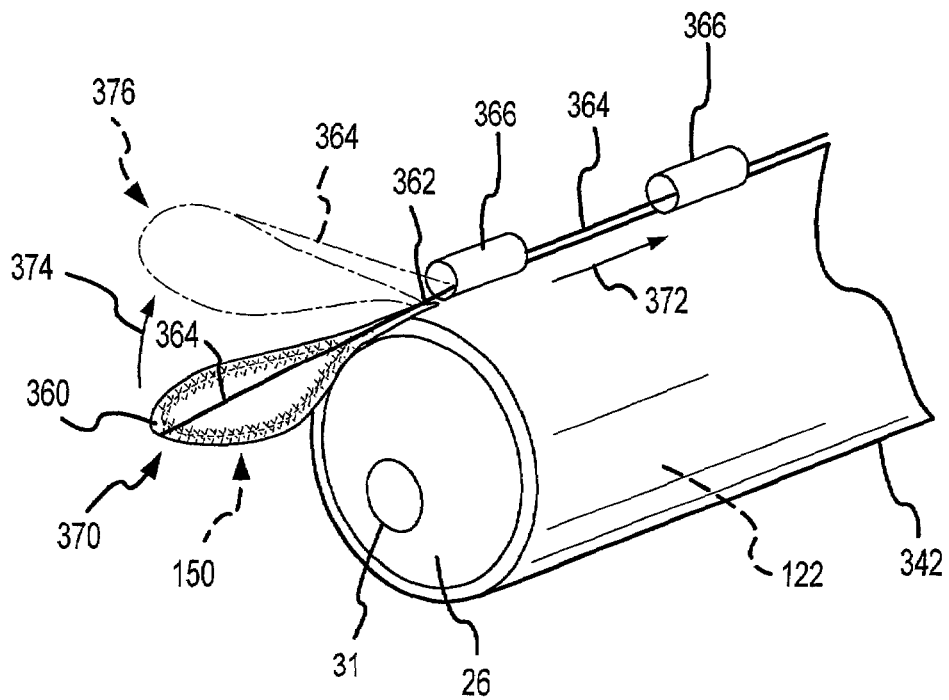
FIG. 9 is an enlarged, partial isometric view of the endoscope assembly of FIG. 8.

FIG. 8 is a partial isometric view of an endoscope assembly 300 in accordance with another embodiment of the invention. FIG. 9 is an enlarged partial isometric view of the endoscope assembly 300 of FIG. 8. In this embodiment, the endoscope assembly 300 includes a sheath assembly 340 having a cover 360 that selectively covers or shields the biopsy sampling device 150. The cover 360 is attached to the body portion 342 at an attachment point 362 proximate the biopsy sampling device 150. An actuation cord 364 is attached to the cover 360 and extends along the body portion 342 of the sheath assembly 340 to the engagement portion 44 of the endoscope 20. The actuation cord 364 is secured to the body portion 342 by a plurality of guide members 366. A handle 368 is attached to the actuation cord 364 proximate the headpiece 28 of the endoscope 20.

In operation, the cover 360 is initially positioned in a first (or non-collecting) position 370 proximate the biopsy sampling device 150, as shown in FIG. 9. In the first position 370, the cover 360 at least partially surrounds and covers the collection member 154 of the biopsy sampling device 150, allowing the endoscope assembly 300 to be more easily inserted into the body cavity of the patient. After insertion, when the operator is ready to obtain a biopsy sample, the operator may pull on the handle 368, retracting the actuation cord 364 in a retraction direction 372 along a longitudinal axis of the body portion 342 of the sheath assembly 340. In turn, the cover 360 is pivotally raised in an opening direction 374 into a second (or collecting) position 376 (see FIG. 8) that is spaced apart from the collection member 154. In the second position 376, the collection member 154 is at least partially exposed so that a biopsy sample may be obtained from the target. The cover 360 may be fabricated from any suitable material, including the same (or a different) elastic or inelastic material as the body portion 342 of the sheath assembly 340. Preferably, the cover 360 has a lower coefficient of friction than the collection member 154 of the biopsy sampling device 150 to ease the task of inserting the assembly 300 into the patient's body cavity.

In one embodiment, the cover 360 is resiliently attached at the attachment point 362 to the body portion 342 and biased in the first position 370 so that the operator must maintain a holding force on the actuation cord 364 to hold the cover 360 in the second position 376. When the holding force is released, the resiliently-attached cover 360 may automatically return to the first position 370. Alternately, the cover 360 may be loosely pinned or hingeably attached so that the cover 360 will remain in the second position 376 without maintaining a holding force on the actuation cord 364. In the latter embodiment, the actuation cord 364 may be replaced with a stiffened actuation member that may be used to both open the cover 360 (by pulling on the actuation member) and close the cover 360 (by pushing on the actuation member), or the cover 360 may be closed by the natural external pressure exerted by the patient's body cavity during withdrawal of the endoscope assembly 300. In either case, after the biopsy sample is obtained, the operator may withdraw the endoscope assembly 300 and biopsy sample from the patient for subsequent analysis.

One may note that the endoscope assembly 300 shown in FIGS. 8 and 9 may preferably be used in conjunction with endoscopes having a rigid, non-flexible insertion tube 122. For example, for some flexible insertion tubes 22, as the operator pulls on the handle 368 to deploy the cover 360 into the collecting position 376 (or pushes on the handle 368 to move the cover 360 into the non-collecting position 370), the forces that are transmitted through the actuation member 364 to the attachment point 362 may be sufficient to cause the flexible insertion tube 22 to bend or articulate in an undesirable manner. On the other hand, for a rigid insertion tube 122, the typical forces transmitted through the actuation member 364 during deployment of the cover 360 do not cause the insertion tube 122 to bend or articulate.

The endoscope assembly 300 provides the above-noted advantages of the previously described embodiments, and may further result in improved ease of inserting and removing the endoscope assembly 300 from the patient. Because the cover 360 at least partially surrounds and covers the collection member 154, the cover 360 may ease the task of inserting the assembly 300 into the patient's body cavity. The cover 360 may also ensure that the collection member 154 does not become occluded with unwanted biopsy samples or undesirable foreign matter during insertion of the assembly 300 which might prevent the collection member 154 from obtaining a suitable biopsy sample from the desired target.

Also, it should be understood that the moveable cover 360 may be used with any type of biopsy sampling device, and is not limited to the biopsy sampling brush shown in FIGS. 8 and 9. For example, in further embodiments, the biopsy sampling device may be a needle (FIG. 7), a forceps, a loop and cup device, a cylindrical cutting device, or any other suitable biopsy sampling apparatus.

Figure 10:
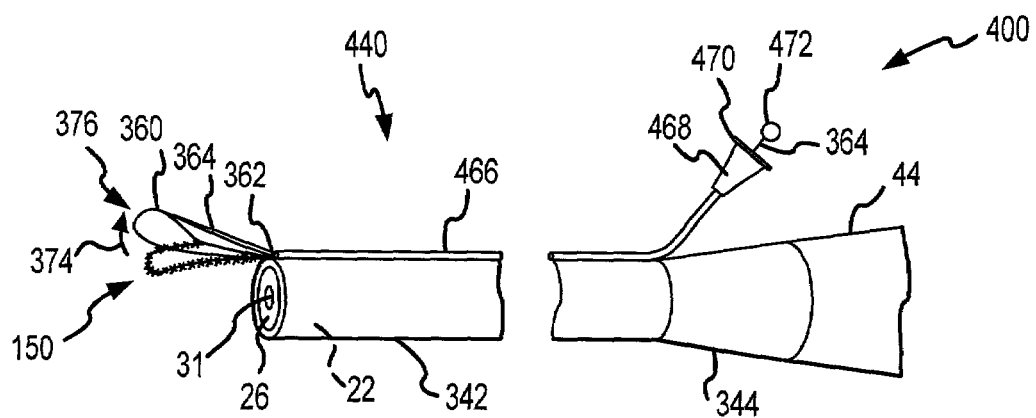
FIG. 10 is a partial isometric view of an endoscope assembly in accordance with still another embodiment of the invention.

FIG. 10 is a partial isometric view of an endoscope assembly 400 in accordance with still another embodiment of the invention. In this embodiment, the endoscope assembly 400 includes a continuous channel 466 (or actuation member guide) attached to the body portion 342 of the sheath assembly 440. A fitting 468 (e.g. a Luer lock fitting) having a flange 470 is attached to the end of the channel 466 that is proximate the engagement portion 44 of the endoscope 20. The actuation member 364 extends through the channel 466, and a loop 472 is attached to the actuation member 364 proximate the flange 470.

In one aspect of operating the endoscope assembly 400, an operator may grasp the fitting 468 and the loop 472, and may actuate the cover 360 by pushing or pulling on the actuation member 364. For example, to move the cover 360 from the non-collecting position 370 (FIG. 9) to the collecting position (FIG. 10), the operator may place a thumb into the loop 472 and one or more fingers on the flange 470 and pull the loop 472 in a direction away from the fitting 468. Conversely, to move the cover 360 back into the non-collecting position 370, the operator may leave the thumb in the loop 472, and may place one or more fingers on the side of the flange opposite from the loop 472, and push the loop 472 in a direction toward the fitting 468. Other methods of actuating the cover 360 of the endoscope assembly 400 are readily conceivable.

The endoscope assembly 400 may advantageously be used with either rigid or flexible insertion tubes. Because the actuation member 364 is housed within the channel 466, when a force is exerted on the insertion tube during actuation of the actuation member 364, an equal but opposite counterbalancing force may be exerted by the operator on the channel. Therefore, undesirable bending or articulation of flexible insertion tubes may be avoided during actuation of the cover 360.

Figure 11:
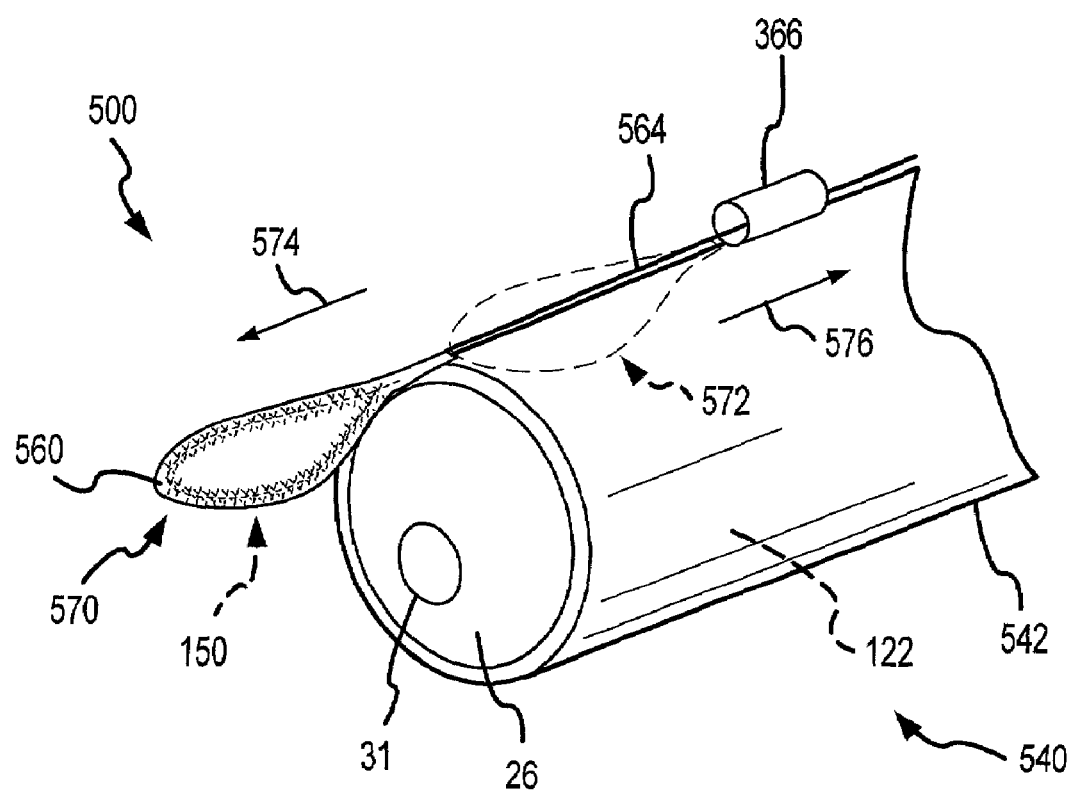
FIG. 11 is an enlarged, partial isometric view of another endoscope assembly in accordance with another embodiment of the invention.

FIG. 11 is a partial isometric view of an endoscope assembly 500 in accordance with another embodiment of the invention. In this embodiment, the endoscope assembly 500 includes a sheath assembly 540 having a cover 560 that slides along the lengthwise or longitudinal axis of the insertion tube 122 to selectively cover and uncover the biopsy sampling device 150. The cover 560 is attached to an actuator 564 that is in turn moveably attached to the body portion 542 of the sheath assembly 540 by one or more guides 366 (FIG. 11) or by a channel 466 (FIG. 10). In this embodiment, the cover 560 is not attached directly to the body portion 542, but rather, is held in the desired position by the actuator 564 (e.g. a rod). Alternately, the cover 560 may be slideably attached to the body portion 542 proximate the biopsy sampling device 150.

In operation, the cover 560 may be moved between a non-collecting position 570 to shield the biopsy sampling device 150, and a collecting position 572 (shown in dashed lines in FIG. 11) to at least partially expose the biopsy sampling device 150. The endoscope operator may move the cover 560 in a forward direction 574 in the manner described above (e.g. by pushing on the actuator 564) to position the cover 560 in the non-collecting position 570. Conversely, to move the cover 560 into the collecting position 572, the operator may move the cover in a rearward direction 576 (e.g. by pulling on the actuator 564) to expose the biopsy sampling device 150. Thus, the above-noted advantages of a sheath having a biopsy sampling device and a cover may be achieved in an assembly that may operate in a smaller, more constricted body passage than other alternate embodiments.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

It should be noted, for example, that alternate embodiments of the invention may be practiced wherein the biopsy sampling device is of a type other than a biopsy brush. Alternate biopsy sampling devices that may be attached directly to a sheath assembly include, but are not limited to, one or more needles, cylindrical cutting devices of the type generally shown in U.S. Pat. No. 4,651,753 issued to Lifton, and loop and cup devices of the type generally shown in U.S. Pat. No. 5,417,697 issued to Wilk et al., U.S. Pat. No. 5,741,271 issued to Nakao et al., which patents are incorporated herein by reference. Such devices may be used independently of, or in conjunction with, one or more actuation cords 364 of the type shown in the accompanying figures which may be connected to the biopsy sampling device to actuate said device to obtain the desired biopsy sample, as more fully described in the above-referenced patents.

Thus, although specific embodiments of, and examples for, the invention are described herein for illustrative purposes, various equivalent modifications are possible within the scope of the invention, as those skilled in the relevant art will recognize. The teachings provided herein can be applied to other apparatus and methods for obtaining biopsy samples using an endoscope sheath assembly having an attached biopsy sampling device, and not just to the embodiments described above and shown in the accompanying figures. Accordingly, the scope of the invention should be determined from the following claims.

The invention claimed is:

1. A sheath and insertion tube assembly comprising:
an endoscope having an insertion tube including a working end;
a sheath including a body portion adapted to completely encapsulate the working end of the insertion rube and having a distal end portion adapted to be proximate the working end when the sheath assembly is positioned on the insertion tube;
a biopsy sampling device attached to the sheath and including a collection member proximate the distal end portion; and
a cover member attached to the sheath proximate the biopsy sampling device, the cover member being moveable between a first position at least partially covering the collection member, and a second position at least partially exposing the collection member.

2. The sheath assembly of claim 1 wherein the cover member includes an actuator extending along at least part of the body portion, the actuator being moveably coupled to the body portion for controllably actuating the cover member.

3. The sheath assembly of claim 1 wherein the cover member is slideably attached to the sheath.

4. The sheath assembly of claim 1 wherein the biopsy sampling device is attached to the body portion.

5. The sheath assembly of claim 1 wherein the sheath includes an enclosed end cap attached to the distal end portion, the biopsy sampling device being attached to the enclosed end cap.

6. The sheath assembly of claim 1 wherein the sheath includes an enclosed end cap attached to the distal end portion, the enclosed end cap having an outer peripheral surface, the biopsy sampling device being attached to the outer peripheral surface.

7. The sheath assembly of claim 1 wherein the collection member comprises a brush member.

8. The sheath assembly of claim 1 wherein the collection member comprises a needle.

9. The sheath assembly of claim 1 wherein the cover member is resiliently biased into the first position.

10. The sheath assembly of claim 1 wherein the cover member is hingeably attached to the sheath.

11. The sheath assembly of claim 1, further comprising a control member coupled to the cover member and extending along the body portion, the control member being moveable for controllably actuating the cover member between a first position and a second position.

12. The sheath assembly of claim 1, further comprising an actuation member coupled to the cover member and extending along the body portion, the actuation member being moveable in a first direction for controllably actuating the cover member into the first position, and being moveable in a second direction for controllably actuating the cover member into the second position.

13. A method for obtaining a biopsy sample from a target within a body, comprising:
providing an endoscope including an insertion tube having a body portion terminating at a distal end;
inserting the insertion tube of the endoscope into a protective sheath that completely encapsulates a major portion of the body portion including the distal end, the sheath having a biopsy sampling device attached thereto that includes a collection member proximate the distal end of the body portion, the sheath further having a cover member proximate the biopsy collection member to at least partially enclose the collection member;
inserting at least part of the body portion of the endoscope including the distal end and the collection member into the body;
actuating the cover member to at least partially expose the collection member engaging the collection member with the target; and
removing the body portion of the endoscope and the collection member from the body.

14. The method of claim 13 wherein providing an endoscopic assembly comprises providing an endoscopic assembly including a sheath having an enclosed distal end and a biopsy the sampling device is attached to the sheath adjacent the enclosed distal end of the insertion tube body portion.

15. The method of claim 13 wherein the biopsy sampling device comprises a biopsy brush attached to the sheath.

16. The method of claim 13 wherein providing an endoscopic assembly comprises providing an endoscopic assembly including a sheath having a cover member proximate the biopsy collection member, and wherein the method further comprises, after inserting at least the collection member into the body, actuating the cover member to at least partially expose the collection member.

17. The method of claim 13 wherein inserting at least the collection member into the body comprises inserting the biopsy sampling device and a distal portion of the endoscope assembly into the body.

18. The method of claim 13 wherein engaging the collection member with the target comprises brushing a biopsy brush against the target.

19. The method of claim 13 wherein providing an endoscopic assembly comprises providing an endoscopic assembly including a sheath having a cover member proximate the biopsy collection member, and wherein the method further comprises, prior to removing the collection member from the body, actuating the cover member to at least partially enclose the collection member.

* * * * *